United States Patent
Pullagurla et al.

(10) Patent No.: US 10,329,325 B2
(45) Date of Patent: Jun. 25, 2019

(54) PROCESS FOR THE PREPARATION OF (S)-4-METHYL-N-((S)-1-(((S)-4-METHYL-1-((R)-2-METHYLOXIRAN-2-YL)-1-OXO-PENTAN-2-YL) AMINO)-1-OXO-3-PHENYLPROPAN-2-YL)-2-((S)-2-(2-MORPHOLINOACETAMIDO)-4-PHENYLBUTANAMIDO) PENTANAMIDE

(71) Applicant: Biophore India Pharmaceuticals Pvt. Ltd, Hyderabad (IN)

(72) Inventors: Manik Reddy Pullagurla, Hyderabad (IN); Jagadeesh Babu Rangisetty, Hyderabad (IN); Mecheril Valsan Nanda Kumar, Hyderabad (IN); Surya Bala Subrahmanyam Pendyala, Hyderabad (IN); Bhaskar Reddy Pitta, Hyderabad (IN)

(73) Assignee: Biophore India Pharmaceuticals Pvt. Ltd, Hyderabad (IN)

( * ) Notice: Subject to any disclaimer, the term of this patent is extended or adjusted under 35 U.S.C. 154(b) by 13 days.

(21) Appl. No.: 15/513,719

(22) PCT Filed: Aug. 29, 2015

(86) PCT No.: PCT/IN2015/050102
§ 371 (c)(1),
(2) Date: Mar. 23, 2017

(87) PCT Pub. No.: WO2016/046843
PCT Pub. Date: Mar. 31, 2016

(65) Prior Publication Data
US 2017/0298093 A1    Oct. 19, 2017

(30) Foreign Application Priority Data

Sep. 24, 2014  (IN) .......................... 4670/CHE/2014

(51) Int. Cl.
| C07K 9/00 | (2006.01) |
| C07K 5/107 | (2006.01) |
| C07K 5/103 | (2006.01) |
| C07C 237/20 | (2006.01) |
| C07D 303/36 | (2006.01) |
| C07K 1/14 | (2006.01) |

(52) U.S. Cl.
CPC .......... *C07K 5/1016* (2013.01); *C07C 237/20* (2013.01); *C07D 303/36* (2013.01); *C07K 1/14* (2013.01); *C07K 5/1008* (2013.01)

(58) Field of Classification Search
None
See application file for complete search history.

(56) References Cited

U.S. PATENT DOCUMENTS

| 7,232,818 B2 | 6/2007 | Smyth et al. |
| 7,417,042 B2 | 8/2008 | Smyth et al. |
| 8,207,297 B2 | 6/2012 | Smyth et al. |
| 8,367,617 B2 | 2/2013 | Phiasivongsa et al. |
| 2005/0256324 A1 | 11/2005 | Laidig et al. |
| 2016/0194354 A1 | 7/2016 | Hoferl-Prantz et al. |
| 2016/0215016 A1 | 7/2016 | Hoferl-Prantz et al. |

FOREIGN PATENT DOCUMENTS

| WO | WO-2009045497 A1 * | 4/2009 | .......... C07D 303/36 |
| WO | 2015032621 A1 | 3/2015 | |
| WO | 2015032622 A1 | 3/2015 | |

OTHER PUBLICATIONS

Smith; Organic Synthesis, Third Edition; Chapter 7; 2010; pp. 1-38; ISBN: 978-1-890661-40-3.
Walsh et al.; "Asymmetric Dihydroxylation (AD) of a,B-Unsaturated Ketones"; Synlett; 1993; pp. 605-606.

* cited by examiner

*Primary Examiner* — Jeanette M Lieb
(74) *Attorney, Agent, or Firm* — The Webb Law Firm

(57) ABSTRACT

Novel methods for preparation of Carfilzomib and intermediates thereof with high stereo selection are reported. The synthetic procedures result in substantially pure Carfilzomib (I).

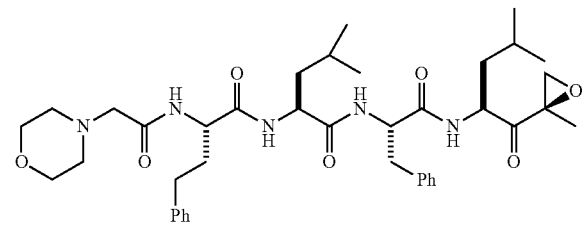

6 Claims, No Drawings

PROCESS FOR THE PREPARATION OF (S)-4-METHYL-N-((S)-1-(((S)-4-METHYL-1-((R)-2-METHYLOXIRAN-2-YL)-1-OXO-PENTAN-2-YL)AMINO)-1-OXO-3-PHENYLPROPAN-2-YL)-2-((S)-2-(2-MORPHOLINOACETAMIDO)-4-PHENYLBUTANAMIDO) PENTANAMIDE

CROSS-REFERENCE TO RELATED APPLICATIONS

This application is the United States national phase of International Application No. PCT/IN2015/050102 filed Aug. 29, 2015, and claims priority to Indian Patent Application No. 4670/CHE/2014 filed Aug. 24, 2014, the disclosures of which are hereby incorporated in their entirety by reference.

BACKGROUND OF THE INVENTION

Field of the Invention

Carfilzomib (I) chemically known as (S)-4-methyl-N—((S)-1-(((S)-4-methyl-1-((R)-2-methyl oxiran-2-yl)-1-oxo-pentan-2-yl)amino)-1-oxo-3-phenylpropan-2-yl)-2-((S)-2-(2-morpholino acetamido)-4-phenylbutanamido) pentanamide is a tetrapeptideepoxyketone and a selective proteasome inhibitor. Chemically it is also known as (2S)—N—((S)-1-((S)-4-methyl-1-((R)-2-methyloxiran2-yl)-1-oxopentan-2-ylcarbamoyl)-2-phenylethyl)-2-((S)-2-(2-morpholinoacetamido)-4-phenylbutanamido)-4-methylpentanamide.

U.S. Pat. Nos. 7,232,818, 8,207,297, 8,367,617, 7,417,042 & US publication 20050256324 reported various processes for the syntheses of Carfilzomib, the contents of which are hereby incorporated as reference in their entirety. The general route of synthesis reported in these patents essentially involves the use of a chiral epoxide III. This epoxide is coupled with tripeptide II to obtain Carfilzomib.

Description of Related Art

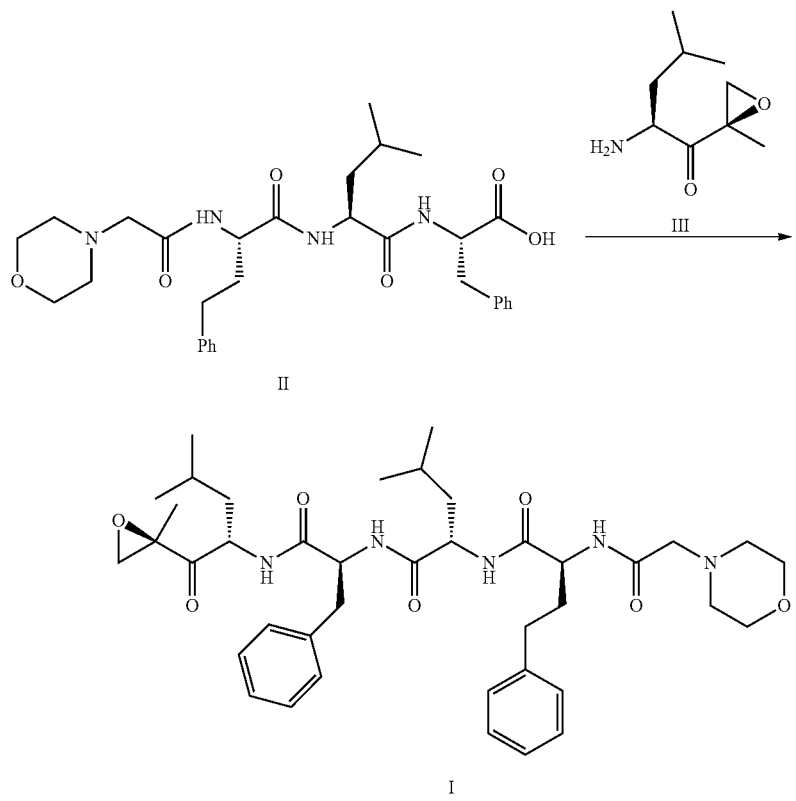

The yield and purity of Carfilzomib synthesized largely depends on the isomeric purity of the epoxide (III).

Therefore the synthesis of a chiral pure epoxide poses a challenge to obtain a substantially pure Carfilzomib.

US 20050256324 application explains two different routes of synthesis for the chiral epoxide.

Prior Art Process 1

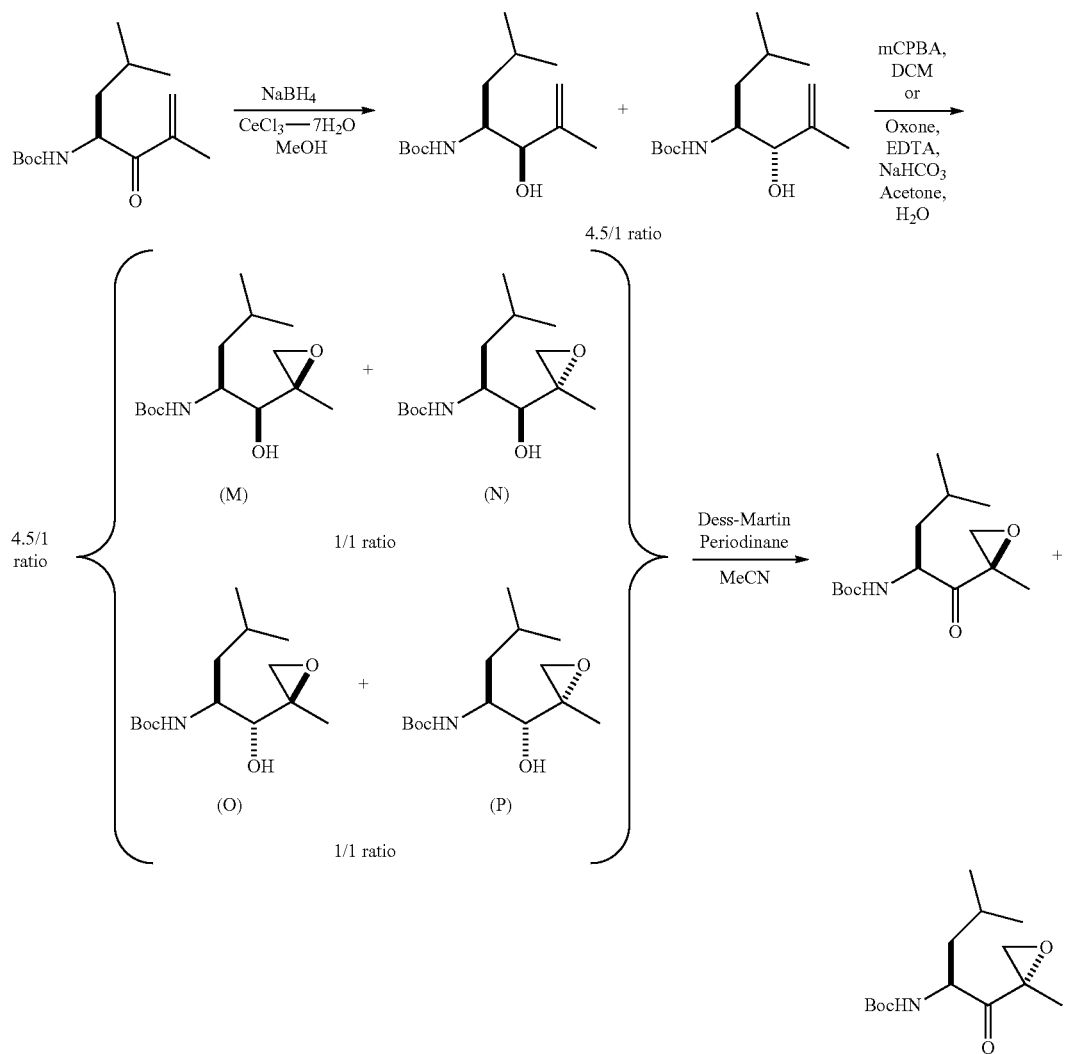

In the first process, a keto alkene was converted into an alcohol derivative, which was subsequently epoxidized to obtain a mixture of diastereomers, from which the desired isomer of epoxide (III)(S)-2-amino-4-methyl-1-((R)-2-methyloxiran-2-yl)pentan-1-one, was isolated by column chromatography.

Prior Art Process 2

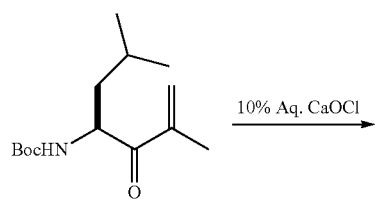

In the second process, the keto alkene was directly subjected to epoxidation using calcium hypochlorite or m-CPBA. The selectivity obtained was in the ratio of 60:40 and the required isomer was once again isolated by column chromatography.

However in either of these cases, the yield of the epoxide III was less, owing to low stereo selection in the reaction (60:40), thereby reducing the final yield of Carfilzomib.

Likewise WO2015032622 A1 involves a Mannich Reaction to prepare Carfilzomib whereas WO2015032621 A1 provides process for preparing epoxy ketones and describes synthesis of Carfilzomib as a 5/1-diastereomeric mixture.

SUMMARY OF THE INVENTION

Accordingly it is an object of the present invention to provide a novel process with high stereo selection for the preparation of substantially pure Carfilzomib.

In one aspect of the invention a method of preparing a substantially pure Carfilzomib, whose isomeric purity is greater than or equal to 99.5% is reported.

It is also an object of the present invention to reduce tedious workups and to prepare Carfilzomib with a high stereo selection.

The first stage of the synthesis involves dihydroxylation of a keto alkene, (S)-tert-butyl (2,6-dimethyl-3-oxo-hept-1-en-4-yl)carbamate (IV) to form a diol, tert-butyl ((2R,4S)-1,2-dihydroxy-2,6-dimethyl-3-oxoheptan-4-yl) carbamate (V). The diol was then protected with a suitable hydroxyl-protecting agent, for example acetyl, to generate a protected diol, (2R,4S)-4-((tert-butoxycarbonyl)amino)-2,6-dimethyl-3-oxoheptane-1,2-diyl diacetate (VI).

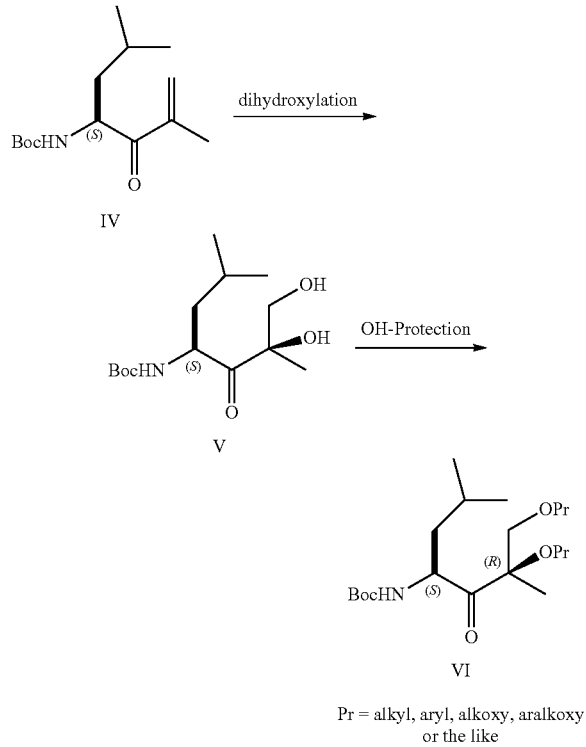

Scheme-1

Pr = alkyl, aryl, alkoxy, aralkoxy or the like

The desired isomer of the diol V can be obtained by chiral dihydroxylation of IV. The hydroxy groups of compound V are protected using hydroxyl-protecting groups to obtain compound VI. When the hydroxyl-protecting group is an acetyl group, compound VI corresponds to (2R,4S)-4-((tert-butoxycarbonyl)amino)-2,6-dimethyl-3-oxoheptane-1,2-diyl diacetate.

The selectivity obtained at this stage is greater than 95% and amounts to yet another aspect of the present invention.

The desired chiral diol isomer VI is then coupled with a tripeptide II in the presence of a coupling agent to generate VII. When the hydroxyl-protecting group is an acetyl group, compound VII corresponds to (4S,7S,10S,13S,15R)-10-benzyl-7,13-diisobutyl-15-methyl-1-morpholino-2,5,8,11,14-pentaoxo-4-phenethyl-3,6,9,12-tetraazahexadecane-15,16-diyl diacetate The protected diol hydroxyl groups of VII were deprotected to obtain a free diol, (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide (VIII).

Alternatively, diol intermediate VIII can also be prepared by the coupling of chiral diol V with tripeptide II.

The primary hydroxyl group of the diol VIII was converted to a leaving group (LG) and the resulting compound IX was then converted to the epoxide by a base mediated cyclization resulting in the formation of substantially pure Carfilzomib (I). When the LG is mesyl, compound IX corresponds to (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl methanesulfonate (IX).

The process is depicted in Scheme-2

Scheme-2

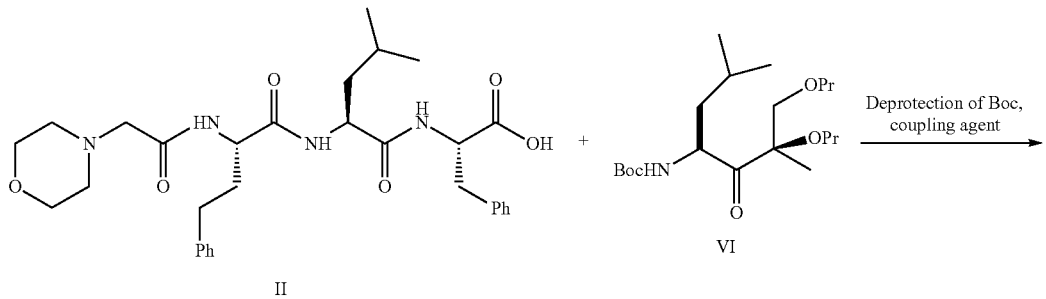

Deprotection of Boc, coupling agent

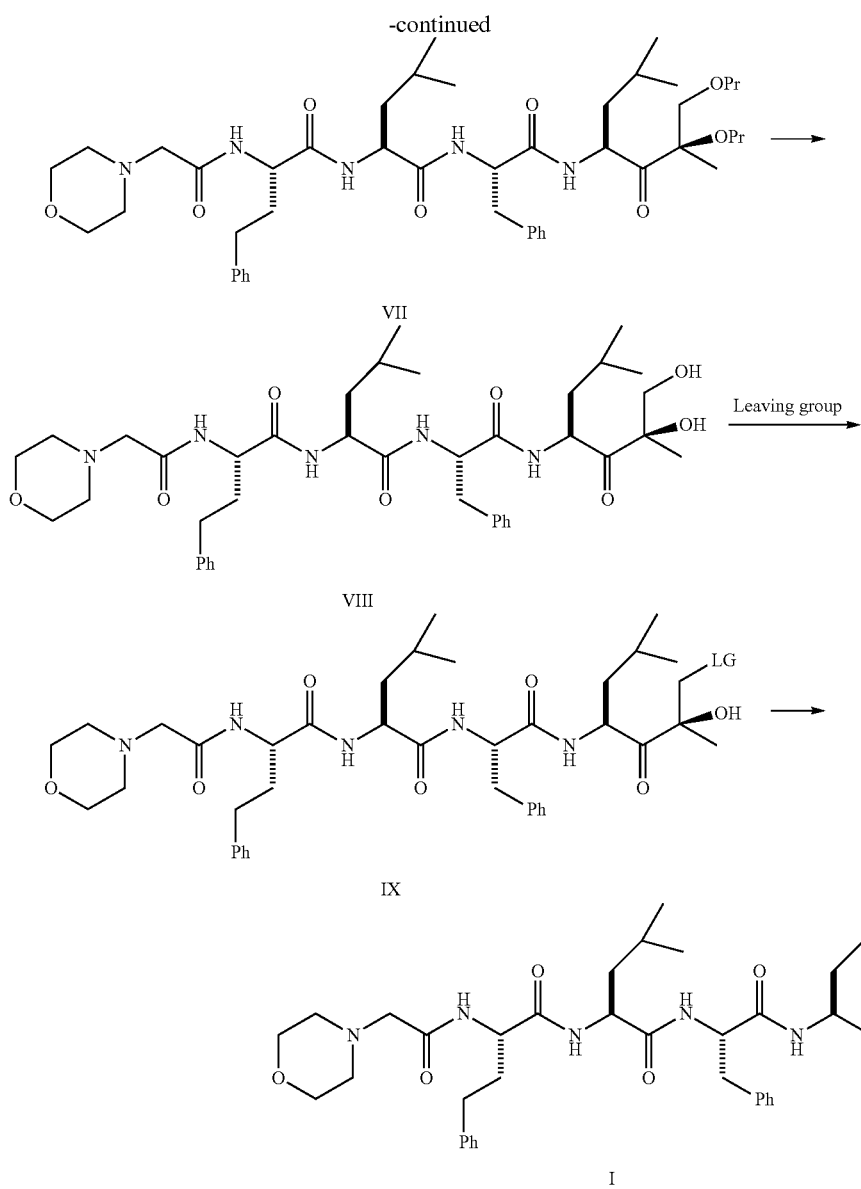
Reaction of II and V Generates VIII:
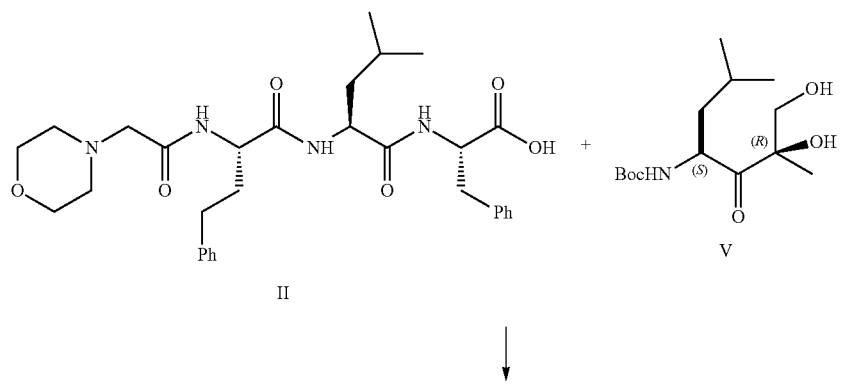

-continued

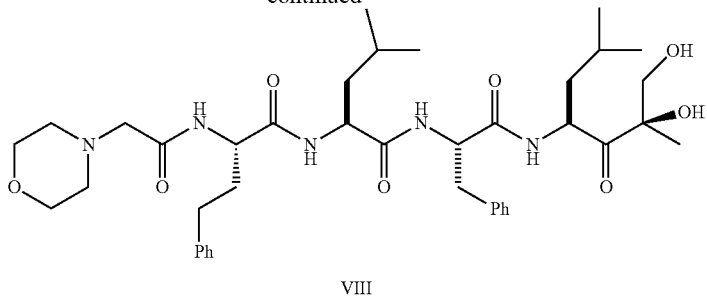

VIII

In yet another aspect of the invention, the inventors have also found an alternate route for the synthesis of substantially pure Carfilzomib (Scheme-3). In this process, the keto alkene IV was first coupled with a tripeptide II in the presence of a coupling agent to generate an intermediate X.

Intermediate X was subjected to dihydroxylation to generate intermediate VIII. The conversion of intermediate VIII to Carfilzomib via the intermediate IX involves the same reaction sequence as in Scheme-2.

Scheme-3

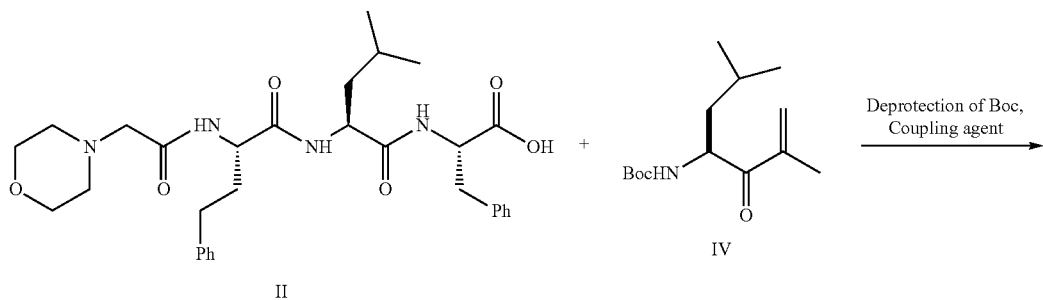

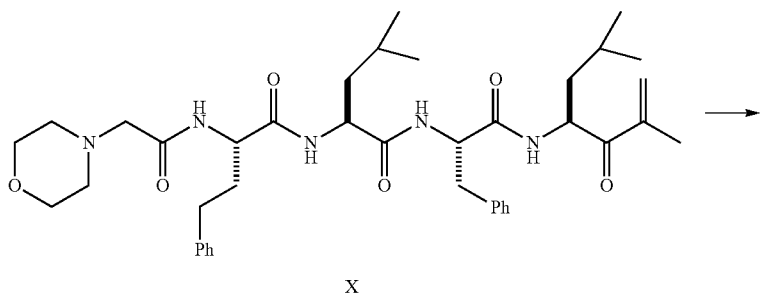

X

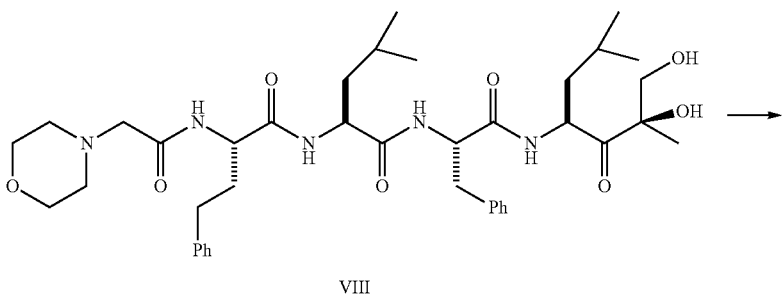

VIII

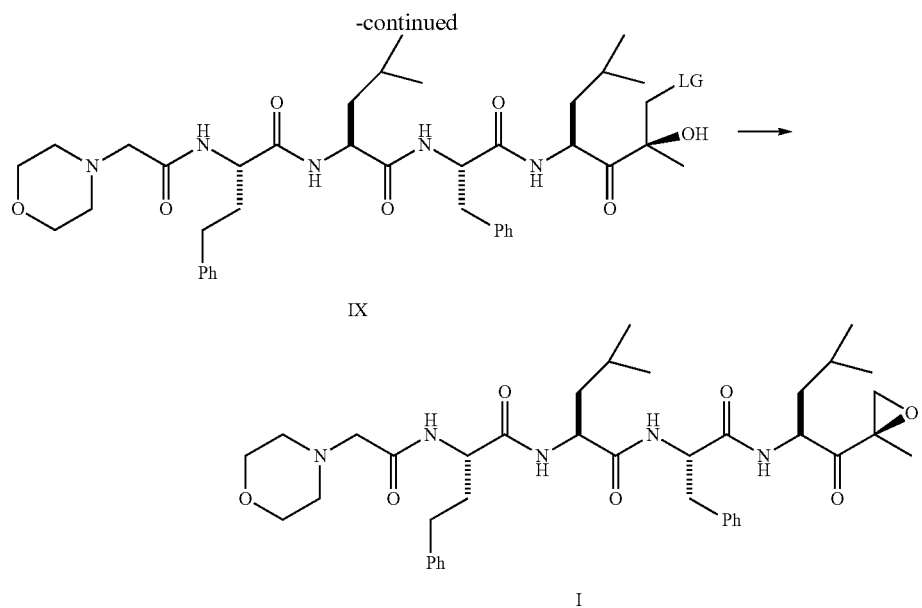

Thus the reported two methods make it possible to synthesize Carfilzomib with greater stereo selection and in higher yield.

DETAILED DESCRIPTION OF THE INVENTION

The two methods for preparing Carfilzomib according to the present invention are characterized by the steps of synthesizing a tetrapeptide intermediate VIII.

Flow Chart Showing Two Methods for Carfilzomib Synthesis

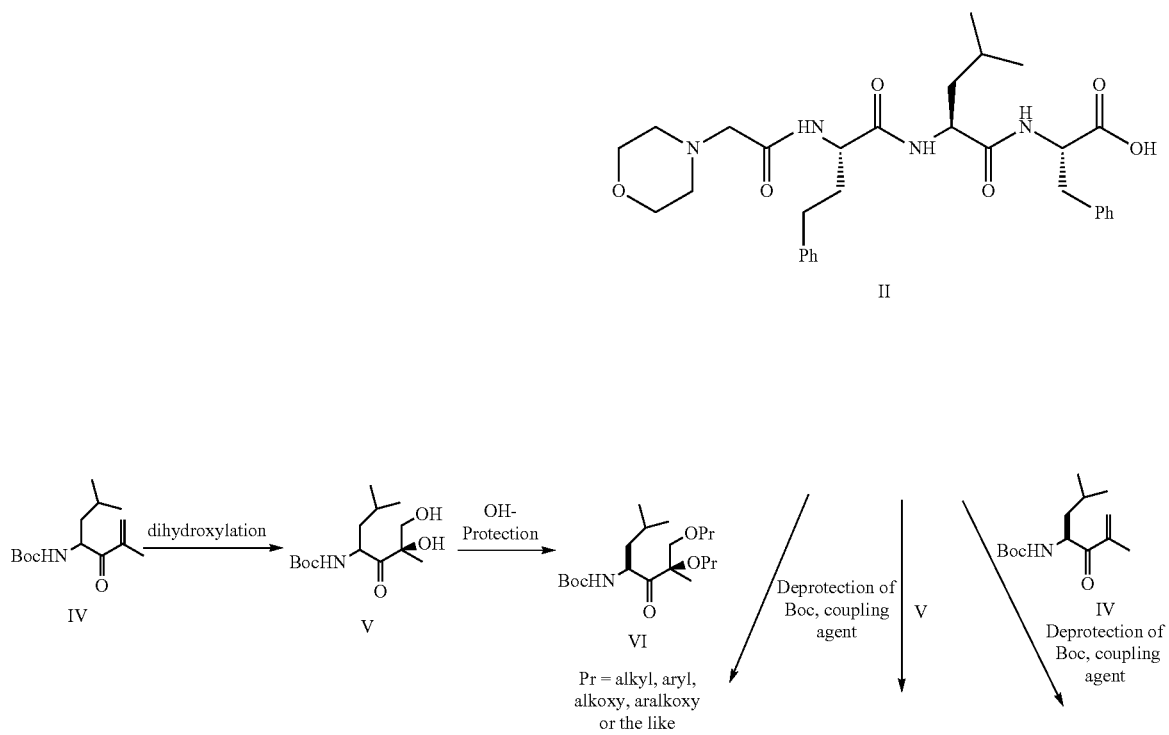

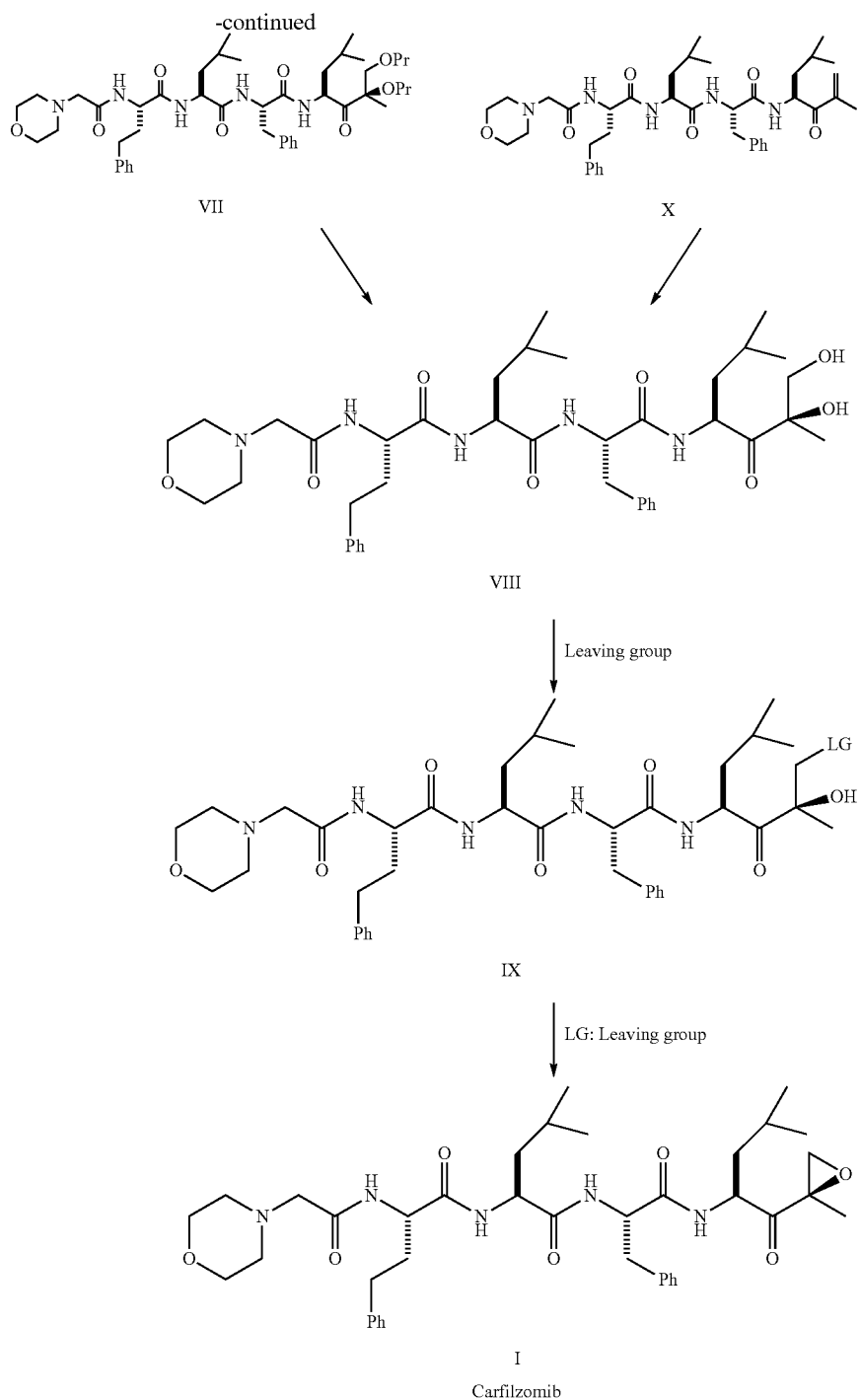

According to the general method of synthesis shown in Scheme-2, the intermediate VIII is prepared from intermediate VII, which in turn is prepared by coupling a chiral diol VI with a tripeptide II. The reaction is performed in an aprotic or a protic solvent or mixtures thereof at temperature ranging from −10 to 30° C., preferably in the presence of a base.

Intermediate VII is deprotected using hydroxyl-deprotecting agents. The reaction is performed in an alcoholic solvent or other protic solvent or mixtures thereof, in the presence of a base, wherein the temperature ranges from −5° C. to 5° C. to generate an intermediate VIII.

Alternatively, compound VIII was prepared by coupling the chiral diol V with tripeptide II in the presence of a suitable coupling agent in a protic or an aprotic solvent or mixtures thereof. Intermediate VIII in subsequent reaction stages is converted to Carfilzomib.

According to the general method depicted in Scheme-3, the intermediate VIII is prepared starting from the ketoalkene IV and involves the following stages:

i) the Ketoalkene IV was boc-deprotected and in-situ coupled with tripeptide II, wherein the reaction is performed in an aprotic solvent or a mixture of aprotic solvents and in the presence of a base and a coupling agent to generate an intermediary compound X.

ii) Compound X is subjected to Cisdihydroxylation using suitable dihydroxylating agents to yield VIII, wherein the solvents employed are protic, aprotic or mixtures thereof.

Compound VIII prepared by any of the above described processes is sufficiently pure to be employed for the next reaction stage. Therefore purification of compound VIII is optional and can be carried out by employing protic solvents like alcohols, aprotic solvents like haloalkane or mixtures thereof, wherein methanol and dichloromethane being the most suitable. Purification of compound VIII can be carried out by treatment with a protic or an aprotic solvent wherein the treatment involves washing with suitable solvent or recrystallizing from suitable solvents wherein the most preferred solvents are methanol, dichloromethane or mixtures thereof.

The required stereo selection in the first method (Scheme-2) is acquired in the early stages when the ketoalkene IV is dihydroxylated to V using chiral dihydroxylating agent such as AD-mix, chiral transition metal complexes, Oxone, KMnO4, OsO4 or the like. The reaction is performed in a protic solvent.

In the second method, the required stereo selection is attained when intermediate X is cis dihydroxylated to VIII using AD-mix, chiral transition metal complexes, Oxone, $KMnO_4$, $OsO_4$ or the like, wherein the most preferred agent being AD-mix.

The primary hydroxyl moiety of VIII is then converted into a leaving group, wherein the reaction is performed at a temperature ranging from −30° C. to 60° C., preferably −5° C.-10° C. to generate IX.

Compound IX under suitable reaction conditions undergoes a nucleophilic substitution reaction in the presence of a base to generate the required epoxide Carfilzomib (I). The reaction is performed in an aprotic solvent, protic solvent or mixtures thereof.

These processes generate substantially pure Carfilzomib with a high stereo selection, which is greater than or equal to 99.5% thus providing the required compound in a very high purity.

Definitions

The following terms shall have for the purpose of this application, including the claims appended hereto, the respective meanings set forth below.

"Hydroxyl or Hydroxy protecting groups", the terms are used synonymously, means those groups that one skilled in the field would recognize as being suitable to protect the —OH substituent on an alkyl or ringed system as described herein and which may be removed under deprotection conditions known to those skilled in the field as set forth. Non-limiting examples of hydroxy protecting groups include ether protecting groups comprising benzyl ethers, silyl ethers, alkyl ethers including methyl ethers, ethyl ethers, propyl ethers, butyl ethers or the like; esters including benzoate, acetate or the like; acetals including MOP, BOM, THP or the like.

The term 'leaving group' (LG) when used herein means those groups that one skilled in the field would recognize as being suitable to substitute the 'OH' moiety (with a leaving group) and includes O-mesyl, O-tosyl, O-acetyl, chloro, bromo, iodo, O-nosyl or the like.

"Coupling agents" means those agents that one skilled in the field would recognize as being suitable to couple a peptide or dipeptide ortripeptide or tetrapeptide or the keto alcohol or the keto alkene or coupling of reactants as described herein, non-limiting examples include DCC, CDI, BOP HOBt/DIC, HBTU, HOBt, HATU, HOAt, PyBOP, TBTU, HCTU, TCTU, HOOBt, 6Cl-HOBt, COMU, DIEA, & EDC.HCl, or the like.

"Dihydroxylating agents" means those reagents that one skilled in the field would recognize as being suitable to introduce 'OH' functional group on the compounds as described herein, non-limiting examples include cis dihydroxylating agents (such as potassium permanganate, osmium tetroxide, AD Mix or the like), chiral dihydroxylating agents such as AD Mix, chiral transition metal complexes, $KMnO_4$, $OsO_4$, Oxone or the like.

"hydroxy deprotecting agents or deprotecting agents" means those reagents that one skilled in the field would recognize as being suitable to remove the protecting groups of a hydroxyl moiety as described herein, non-limiting examples being inorganic bases like potassium hydroxide, lithium hydroxide, sodium hydroxide, potassium carbonate, sodium carbonate or the like.

"Boc deprotection" means removal of the Boc moiety which is protecting the amino group and the suitable reagents for the purpose are those that one skilled in the field would recognize as being suitable to remove the Boc protection on the amino moiety as described herein, non limiting examples being organic and inorganic acids wherein, HCl and Trifluroacetic acid are the most preferred.

The term "base" when used herein includes alkali hydroxides, alkoxides, alkali hydrides, or compounds such as amine derivatives, carbonates or the like, for example potassium hydroxide, lithium hydroxide, sodium hydroxide, potassium carbonate, sodium carbonate, lithium carbonate, alkoxides like sodium methoxide, sodium ethoxides, potassium tert.butoxide, sodium tert.butoxide, organic bases such as triethyl amine, pyridine, DMAP, NaHMDS, LiHMDS, DIPA, pyrrolidine or the like.

The term 'aprotic solvent' when used herein includes dichloromethane, chloroform, dichloroethane acetonitrile, dimethyl sulphoxide (DMSO), Tetrahydrofuran (THF), dimethyl formamide (DMF), Ethyl acetate, acetone, n-Methyl pyrrolidine (NMP), dimethyl acetamide (DMA), diethyl ether, MTBE, Toluene, Cyclohexanes, hexanes, dioxanes or the like.

The term 'protic solvent' when used herein includes alcohols like Methanol, ethanol, Isopropanol, n-propanol, n-butanol; Water; formic acid, nitromethane, acetic acid and The term 'alcoholic solvent' when used herein includesmethanol, ethanol, n-propanol, n-butanol, isopropyl alcohol, water or the like.

The term solvent when used herein includes aprotic, protic, or mixtures thereof.

Reagent Definitions

| | |
|---|---|
| MOP | 2-Methoxy-2-propyl (MOP) ethers |
| BOM | Benzyloxymethylacetal |
| THP | Tetrahydropyranylacetal |
| BOC | Tert-butyloxycarbonyl (as protecting group) |
| DCC | 1,3-dicyclohexylcarbodiimide |
| BOP | Benzotriazol-l-yl-oxy-tris(dimethylamino)phosphonium hexafluorophosphate |
| DIC | 1,3-Diisopropylcarbodiimide |

| | |
|---|---|
| HBTU | 2-(1H-benzotriazol-1-yl)-1,1,3,3-tetramethyluronium hexafluorophosphate |
| HOBt | Hydroxy benzotriazole |
| CDI | 1,1'-Carbonyldiimidazole |
| HATU | 1-[Bis(dimethylamino)methylene]-1H-1,2,3-triazolo(4,5-b)pyridinium 3-oxid hexafluorophosphate |
| HOAt | 1-hydroxy-7-azabenzotriazole |
| PyBOP | benzotriazol-1-yl-oxytripyrrolidinophosphonium hexafluorophosphate |
| TBTU | 0-(Benzotriazol-1-yl)-N,N,N',N'-tetramethyluronium tetrafluoroborate |
| HCTU | 1H-Benzotriazolium 1-[bis(dimethylamino)methylene]-5-chloro,hexafluorophosphate(1-),3-oxide |
| TCTU | 0-(6-Chlorobenzotriazol-1-yl)-N,N,N',N'-tetramethyluronium tetrafluoroborate |
| HOOBt | 3-hydroxy-1,2,3-benzotriazin-4-one |
| 6Cl-HOBt | 1-Hydroxy-6-chloro-benzotriazole |
| COMU | 1-Cyano-2-ethoxy-2-oxoethylidenaminooxy)dimethylamino-morpholino-carbenium hexafluorophosphate |
| DIEA | N,N-Diisopropylethylamine |
| EDC•HCl | 1-Ethyl-3-(3-dimethylaminopropyl)carbodiimide hydrochloride |
| KMnO$_4$ | Potassium permanganate |
| OsO$_4$ | Osmium tetroxide |
| DMAP | 4-Dimethylaminopyridine |
| NaHMDS | Sodium bis(trimethylsilyl)amide |
| LiHMDS | Lithium bis(trimethylsilyl)amide |
| DIPA | Diisopropylamine |
| TFA | Trifluoro acetic acid |
| DCM | Dichloromethane |
| DM water | Demineralized water |
| MTBE | Methyl tertiary butyl ether |
| AD MIX (AD mix-β) | Mixture contains: (DHQD)$_2$PHAL (Cat. No. 392731) 0.0016 mole Potassium carbonate, powder 0.4988 mole Potassium ferricyanide 0.4988 mole Potassium osmate dihydrate 0.0007 mole |

The following examples further illustrate the present invention, but should not be construed in anyway as to limit its scope.

Example 1

Preparation of (S)-tert-butyl (2,6-dimethyl-3-oxo-hept-1-en-4-yl)carbamate (IV) is schematically represented below Scheme-4

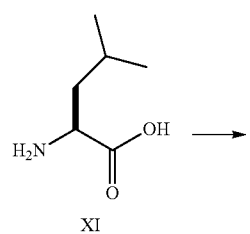

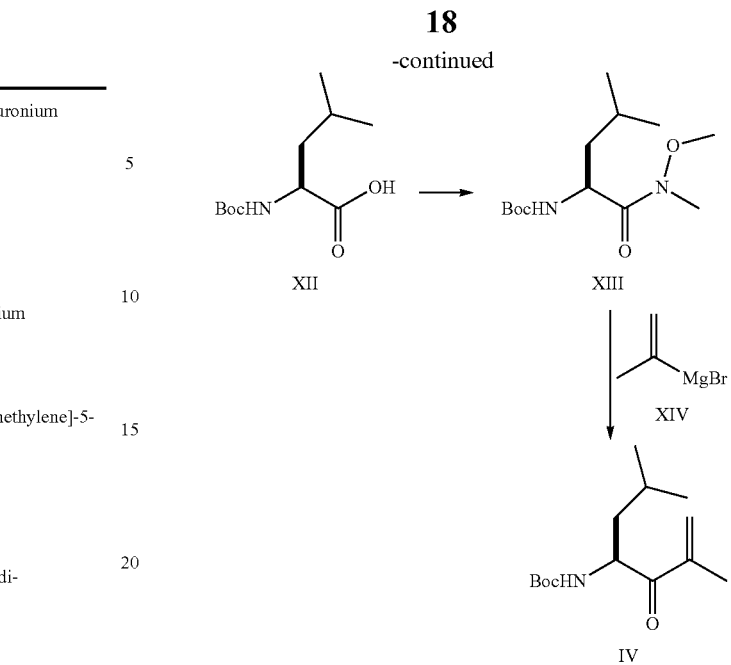

a. Compound (XII) (S)-2-((tert-butoxycarbonyl)amino)-4-methylpentanoic acid 1.0 g of L-leucine (XI) was dissolved in 8 ml of acetone. 4 ml of 1 N sodium hydroxide solution was added to the reaction mass and cooled to 0-5° C. 1.09 Eq. of Di-t-butyl bicarbonate was added and stirred for 2-3 hrs. The pH of the reaction mass was adjusted to 2.0-3.0 using 1N hydrochloric acid and extracted with dichloromethane. The organic layer was distilled off under vacuum to get 90% of title compound.

b. Compound (XIII) (S)-tert-butyl (1-(methoxy(methyl)amino)-4-methyl-1-oxopentan-2-yl)carbamate 5.0 g of (S)-2-((Tert-butoxycarbonyl)amino)-4-methylpentanoic acid (XII) was dissolved in 40 ml of dichloromethane. 1.27 Eq. of Isobutyl formate was added to the reaction mass and cooled to −20° C. 1.09 Eq. of 4-Methylmorpholine was added over a period of 20-30 min at −20° C. A mixture of dichloromethane, N,O-Dimethylhydroxylamine hydrochloride and triethylamine was prepared in a separate flask and added to the above solution. The reaction mass is maintained at 25-30° C. for 2-3 hrs. The organic layer is separated and washed with sodium bicarbonate followed by sodium chloride solution. The resulting solvent layer was distilled off under vacuum to get 98% of title compound XIII.

c. Compound (IV) (S)-tert-butyl (2, 6-dimethyl-3-oxohept-1-en-4-yl)carbamate 4.0 g of (S)-Tert-butyl (1-(methoxy (methyl)amino)-4-methyl-1-oxopentan-2-yl)carbamate (XIII) was dissolved in 32 ml of THF and cooled to −78° C. 10 ml of Isopropenylmagnesium bromide (XIV) was added to the reaction mass and stirred for 10-12 hrs at 0-5° C. The reaction mass was extracted with ethyl acetate and the solvent was distilled off under vacuum to get 65% of title compound.

Example 2: Compound (V) tert-butyl ((2R,4S)-1,2-dihydroxy-2,6-dimethyl-3-oxoheptan-4-yl)carbamate 1.0 g of (Boc-Leu-ketoAlkene) (S)-tert-butyl (2,6-dimethyl-3-oxohept-1-en-4-yl)carbamate (IV) and 15 ml of t-butanol and water (1:1) was charged into a dry RB flask and cooled to 0-5° C. 5 g of AD mix-β, dissolved in 10 ml of water was slowly added to the reaction mixture and stirred for 24 hrs at the same temperature. The reaction mixture was quenched by adding 40 ml of sodiumthiosulphate solution. The reaction mixture was then extracted with ethyl acetate and the organic layer was collected and dried over sodium sulphate. The excess solvent is distilled off to obtain a crude mass which was treated with hexane at 25-30° C. and stirred for 20-30 minutes. The thus obtained solid was filtered under vacuum to give compound V in 55% yield.

Example 3: Compound (VI) (2R,4S)-4-((tert-butoxycarbonyl)amino)-2,6-dimethyl-3-oxoheptane-1,2-diyl diacetate 1.0 g of compound V was dissolved in 15 ml of dichloromethane and the reaction mixture is cooled to 0-5° C. 8 Eq. of acetic anhydride, 8 Eq. of pyridine and catalytic amount of DMAP was added to the reaction mixture and stirred for 1 hr at the same temperature. After completion of the reaction, the reaction mixture is quenched with water and the product was extracted by standard work up procedure and the title compound VI was isolated.

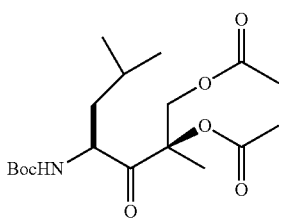

VI when Pr=acetyl

Example 4: Compound (VII) (4S,7S,10S,13S,15R)-10-benzyl-7,13-diisobutyl-15-methyl-1-morpholino-2,5,8,11,14-pentaoxo-4-phenethyl-3,6,9,12-tetraazahexadecane-15,16-diyl diacetate 0.6 g of compound VI was dissolved in 10 ml of dichloromethane and the reaction mixture was cooled to 0-5° C. 3 ml of 80% TFA/DCM was added to the reaction mixture and maintained for 30 minutes at the same temperature. After completion of the boc-deprotection, the solvent was distilled under reduced pressure. To the reaction mixture, 1 Eq. of the peptide intermediate II, 10 ml of DMF, 1.5 Eq. of HOBt and 4 Eq. DIEA were added successively at 0-5° C. 1.5 Eq. of BOP was added to the reaction mixture and stirring was continued at 0-5° C. for 3-5 h. The reaction was monitored by TLC and after completion of the reaction; water was added to the reaction mixture. The product was extracted with ethyl acetate and the pure product VII, as a diacetylated product was isolated by recrystallization from ethylacetate.

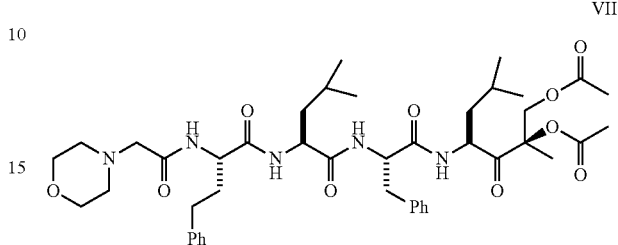

VII

When Pr=acetyl

Example 5: Compound (VIII) (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide 0.6 g of diacetylated derivative VII was dissolved in 10 ml of methanol and the reaction mixture was cooled to 0-5° C. 3 Eq. of NaOH was added to the reaction mixture and stirred for 1 h at 0-5° C. After completion of the reaction, water was added to the reaction mixture and the pH was adjusted to 3 with 1N HCl. The product was then extracted with dichloromethane and the organic layer was dried over sodium sulfate. The solvent was removed under reduced pressure and product VIII was isolated.

Example 6: Compound (VIII) (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide 3.0 g of compound V was added to a mixture of dichloromethane and trifluoro acetic acid at 0-5° C. The reaction mass was stirred for 1 hr at 0-5° C. and the solvent was distilled off under vacuum at below 40° C. The crude reaction mass was stripped off with dichloromethane followed by hexane and dimethyl formamide was added to the reaction mass. The reaction mass was cooled to 0-5° C. and N,N-diisopropylamine was added. The reaction mass was stirred for further 5-10 minutes, 1.0 Eq. of compound II, 1.32 Eq. of hydroxybenzotriazole and 4.7 Eq. of BOP were added at 0-5° C. The reaction mass was maintained at 0-5° C. for 10-12 hrs. After completion of reaction, the reaction mass was quenched with water, filtered and the solid obtained was washed with DM water to get the title compound in 40% yield.

Example 7: Preparation of (S)-2-((S)-4-methyl-2-((S)-2-(2-morpholinoacetamido)-4-phenylbutanamido) pentanamido)-3-phenylpropanoic acid (Compound II) is schematically represented below
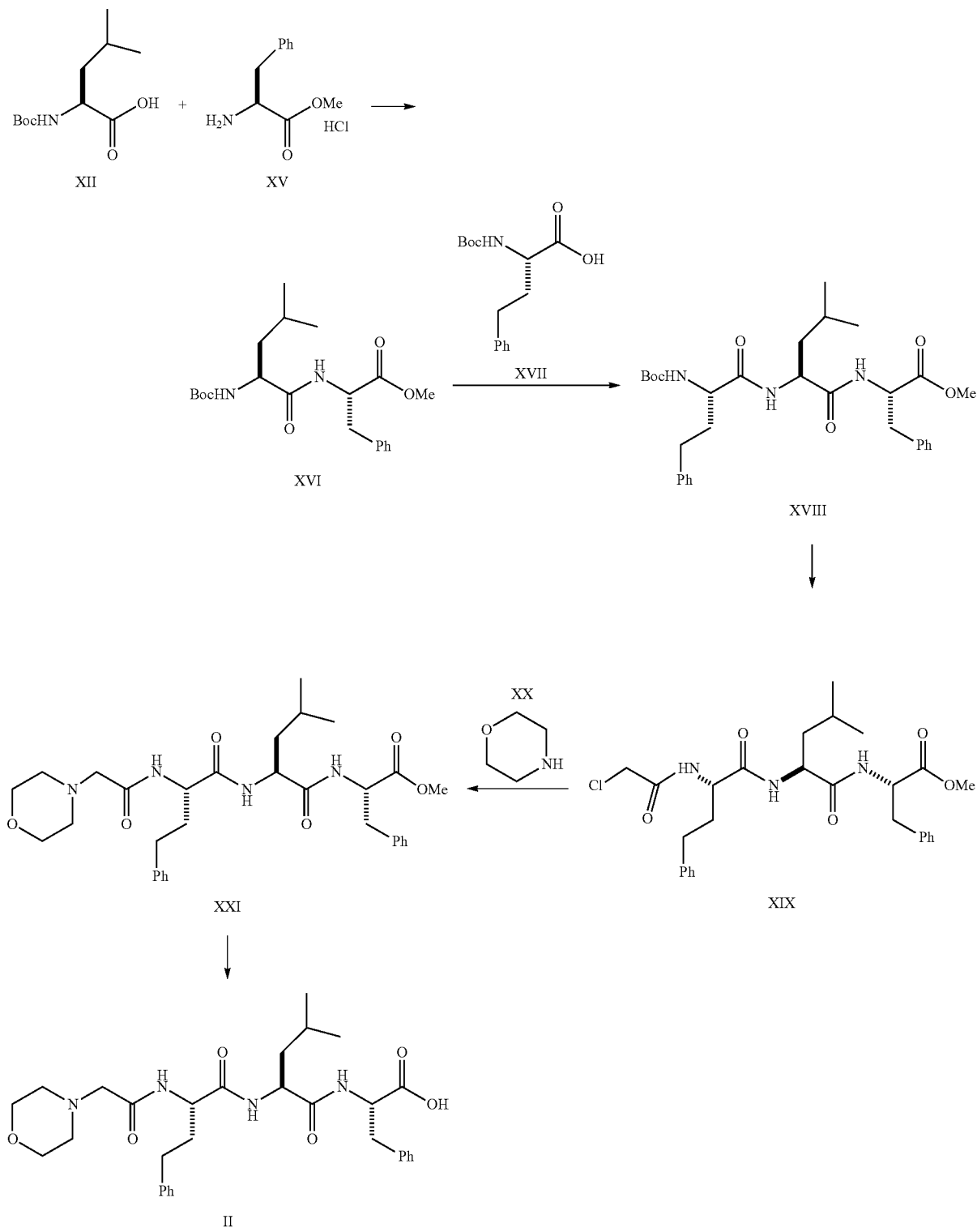
Scheme-5 a. Compound (XVI) (S)-methyl 2-((S)-2-((tert-butoxycarbonyl) amino)-4-methyl pentanamido)-3-phenyl propanoate 10.3 g of (S)-Methyl 2-amino-3-phenylpropanoate hydrochloride (XV) was dissolved in 150 ml of dichloromethane under nitrogen atmosphere. 1.89 Eq. of triethyl amine was added and stirred for 1 hr at 25-30° C. The reaction mass was cooled to −10 to −15° C. and kept aside. In a separate RB flask 10 g of (S)-2-((tert-butoxycarbonyl) amino)-4-methyl-pentanoic acid (XII) was dissolved in 50 ml of dichloromethane and cooled to −20 to −15° C. 2.0 Eq. of 4-Methylmorpholine and 1.4 Eq. of Isobutyl chloroformate were added at −20 to −15° C. To the reaction mass the above solution kept at −10 to −15° C. was added and stirred for 2-3 hrs at 0-5° C. 150 ml of DM water was added to the reaction mass and extracted with Dichloromethane. The organic layer was washed with water, 1 N hydrochloric acid solution, DM water followed by sodium bicarbonate solution and sodium chloride solution. The organic layer is then dried over sodium sulphate and distilled under vacuum. 100 ml of hexane was added to the crude and stirred for 60 minutes at 25-30° C. The solid is filtered and washed with hexane. The obtained solid was suck dried under vacuum to get 74% of the title compound.

b. Compound (XVIII) (6S, 9S, 12S)-methyl 12-benzyl-9-isobutyl-2, 2-dimethyl-4, 7, 10-trioxo-6-phenethyl-3-oxa-5, 8, 11-triazatridecan-13-oate 10 g of (S)-Methyl 2-((S)-2-((tert-butoxycarbonyl) amino)-4-methyl pentanamido)-3-phenyl propanoate (XVI) was dissolved in 5 ml of dichloromethane and 30 ml of trifluoro acetic acid. The reaction mixture was stirred for 10-15 min at −5 to 0° C. and further stirred at 25-30° C. for 2-3 hrs. After completion of reaction, the reaction mass was distilled under vacuum and the residue is stripped off with dichloromethane. 80 ml of dichloromethane was added and pH adjusted to 7-8 with N,N-Diisopropylethylamine at 0 to −5° C. 1.12 Eq. of Boc-L-Homophenyl alanine dissolved in 40 ml of DMF was added to the reaction mass. 1.8 Eq. of Hydroxybenzotriazole and 1.6 Eq. of (Benzotriazol-1-yloxy)tris(dimethylamino) phosphonium hexafluorophosphate were added and stirred for 2-3 hrs at −5 to 0° C. 350 ml of cold DM water and 200 ml of dichloromethane were added to the reaction mass and the aqueous layer was extracted with dichloromethane. The organic layer was washed with DM water, 1 N hydrochloric acid followed by Sodium bicarbonate solution. Organic layer was distilled off under vacuum, 100 ml of hexane was added to the crude and stirred for 1 hr at 25-30° C. The solid was filtered and dried under vacuum. The obtained solid was taken in (95:5) ratio of ethanol and water and heated at 70-75° C. for 30 minutes. The reaction mass was cooled to 25-30° C. and further to −5 to 0° C. for 60-90 minutes. The solid was filtered and washed with mixture of ethanol and water to get the title compound in 85% yield.

c. Compound (XIX) (S)-Methyl 2-((S)-2-((S)-2-(2-chloroacetamido)-4-phenylbutanamido)-4-methyl-pentanamido)-3-phenylpropanoate 10 g of (6S, 9S, 12S)-Methyl 12-benzyl-9-isobutyl-2, 2-dimethyl-4, 7, 10-trioxo-6-phenethyl-3-oxa-5, 8, 11-triazatridecan-13-oate (XVIII) was dissolved in 5 ml of dichloromethane and 30 ml of trifluoro acetic acid at −5 to 0° C. The reaction mass is stirred for 10-15 minutes at −5 to 0° C. and for 2-3 hrs at 25-30° C. After completion of reaction, solvent was distilled off under vacuum. 110 ml of dimethylformamide was added to the crude reaction mass which was slowly added to 2.09 Eq. of Chloroacetyl chloride at −5 to 0° C. under nitrogen atmosphere. The pH of the reaction mass was adjusted to 7.0-8.0 with 8.75 Eq. of N,N-Diisopropylethylamine at −5 to 0° C. and stirred for 2-3 hrs. 1200 ml of DM water is added, the aqueous layer is separated and 100 ml of hexane was added. The solid is filtered and dried under vacuum to get the title compound in 85% yield.

d. Compound (XX) (S)-methyl 2-((S)-4-methyl-2-((S)-2-(2-morpholinoacetamido)-4-phenylbutanamido) pentanamido)-3-phenylpropanoate 8.0 g of (S)-Methyl 2-((S)-2-((S)-2-(2-chloroacetamido)-4-phenylbutanamido)-4-methylpentanamido)-3-phenylpropanoate (XIX) was dissolved in 160 ml of THF, 0.4 Eq. of Potassium iodide and 2.2 Eq. of Morpholine were added. The reaction mass was stirred for 3-4 hrs at 25-30° C. After completion of reaction 500 ml of sodium chloride and 400 ml of ethyl acetate were added to the reaction mass. The reaction mass was extracted with ethyl acetate and the solvent was distilled off under vacuum. Hexane was added to the crude and stirred for 20-30 min at 25-30° C. The solid was filtered and dried under vacuum to get the title compound in 85% yield.

e. Compound (II) (S)-2-((S)-4-methyl-2-((S)-2-(2-morpholinoacetamido)-4-phenylbutanamido) pentanamido)-3-phenylpropanoic acid 7.0 g of (S)-Methyl-2-((S)-4-methyl-2-((S)-2-(2-morpholinoacetamido)-4-phenylbutanamido) pentanamido)-3-phenylpropanoate (XXI) was dissolved in 56 ml of methanol and 21 ml of DM water. The reaction mixture was cooled to 0-5° C. and 5.0 Eq. of lithium hydroxide monohydrate was added and stirred for 3-4 hrs at 0-5° C. After completion of reaction 500 ml of ammonium chloride solution was added and the solvent was distilled under vacuum at 60° C. The pH of the obtained crude was adjusted to 2.0-3.0 using 1 N Hydrochloric acid and aqueous layer was extracted with dichloromethane. The extracted organic layer was washed with sodium chloride followed by DM water. The solvent was distilled off under vacuum and the crude was stripped off with ethyl acetate. Methanol was added to the crude and cooled to 0-5° C. To this, methyl tertiary butyl ether was added and stirred for 2-3 hrs at 0-5° C. The solid is filtered and dried under vacuum to get the title compound in 90% yield.

Example 8: Compound (X) (S)—N—((S)-1-(((S)-2, 6-dimethyl-3-oxohept-1-en-4-yl)amino)-1-oxo-3-phenylpropan-2-yl)-4-methyl-2-((S)-2-(2-morpholinoacetamido)-4-phenylbutanamido) pentanamide 6.0 g of compound IV was dissolved in 10 ml of dichloromethane and the reaction mixture was cooled to 0-5° C. 3 ml of 80% TFA/DCM was added to the reaction mixture and maintained for 30 minutes at the same temperature. After completion of the boc-deprotection, the solvent was distilled under reduced pressure. To the reaction mixture, 1 Eq. of the peptide intermediate II, 10 ml of DMF, 1.5 equiv. of HOBt and 4 equiv. DIEA were added successively at 0-5° C. 1.5 Eq. of BOP was added to the reaction mixture and stirring was continued at 0-5° C. for 3-5 h. The reaction was monitored by TLC and after completion of the reaction; water was added to the reaction mixture. The product was extracted with ethyl acetate and the pure product X was isolated by recrystallization from ethyl acetate.

Example 9: Compound (VIII) (S)—N—((S)-1-(((2R,4S)-1,2-dihydroxy-2,6-dimethyl-3-oxoheptan-4-yl)amino)-1-oxo-3-phenylpropan-2-yl)-4-methyl-2-((S)-2-(2-morpholinoacetamido)-4-phenylbutanamido)pentanamide 1.0 g of (S)—N—((S)-1-(((S)-2,6-Dimethyl-3-oxohept-1-en-4-yl)amino)-1-oxo-3-phenylpropan-2-yl)-4-methyl-2-((S)-2-(2-morpholinoacetamido)-4-phenylbutanamido)pentanamide (X) and 15 ml of t-butanol and water (1:1) was charged into a dry RB flask and cooled to 0-5° C. 5 g of AD mix-β, dissolved in 10 ml of water was slowly added to the reaction mixture and stirred for 24 hr at the same temperature. The reaction mixture was quenched by adding 40 ml of sodium thiosulphate solution. The reaction mixture was then extracted with ethyl acetate and the organic layer was collected and dried over sodium sulphate. The solvent was evaporated under vacuum to give compound VIII.

Example 10: Compound (IX) (4S,7S,10S,13S,15R)-10-benzyl-15-hydroxy-7,13-diisobutyl-15-methyl-1-morpholino-2,5,8,11,14-pentaoxo-4-phenethyl-3,6,9,12-tetraazahexadecan-16-yl methanesulfonate (wherein the LG is mesyl)

0.6 g of the compound VIII was dissolved in 10 ml dichloromethane and the reaction mixture was cooled to 0-5° C. 4 Eq. of triethyl amine and 2 Eq. pyridine was added to the reaction mixture and stirred for 10 minutes. To the reaction mixture, 1 Eq. of mesyl chloride was added drop wise and stirring was continued for another 1 h. After completion of the reaction, water was added and the product was extracted with dichloromethane. The organic layer was collected and dried over anhydrous sodium sulfate and distilled under vacuum to give monomesylated product IX in 90% yield.

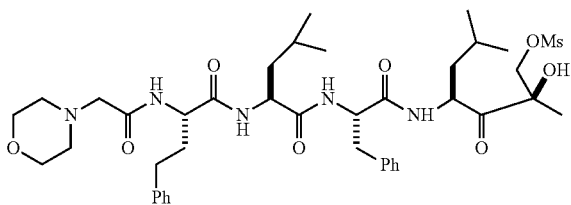 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@](C)(O)COS(C)(=O)=O]

where LG is mesyl

Example 11: Compound (I) (S)-4-methyl-N—((S)-1-(((S)-4-methyl-1-((R)-2-methyl oxiran-2-yl)-1-oxopentan-2-yl)amino)-1-oxo-3-phenylpropan-2-yl)-2-((S)-2-(2-morpholino acetamido)-4-phenylbutanamido)pentanamide 1.0 g of compound IX was dissolved in 10 ml of methanol and the reaction mass is cooled to 0-5° C. 1 Eq. of potassium carbonate was added to the reaction mixture and stirring was continued for another 1 h at the same temperature. After completion of the reaction, the reaction mixture was quenched with water and the pH was adjusted to 3 with 1 N HCl. The product was extracted with dichloromethane and the organic layer was dried over anhydrous sodium sulfate. Solvent was removed under reduced pressure and Carfilzomib (I) was isolated with 70% yield with isomeric purity>99.5%.

We claim:
1. A process for the preparation of Carfilzomib (I),

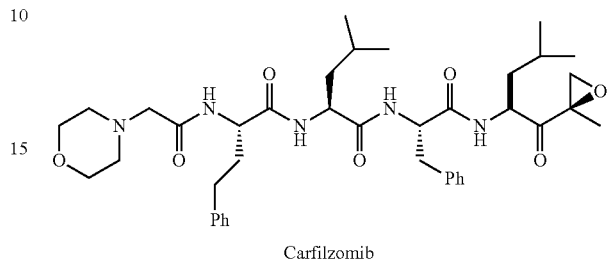

Carfilzomib comprising:
i. coupling of tripeptide of formula II

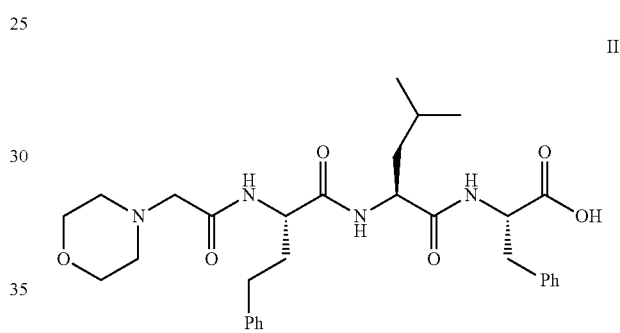

with a ketoalkene of formula IV

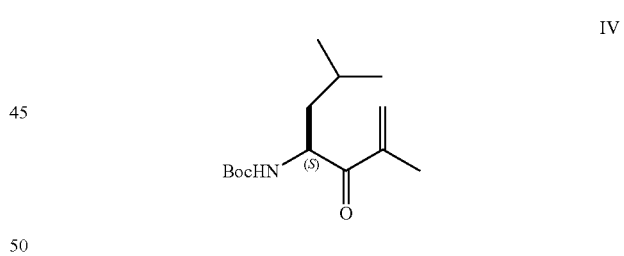

in the presence of a coupling agent to isolate an intermediary compound X

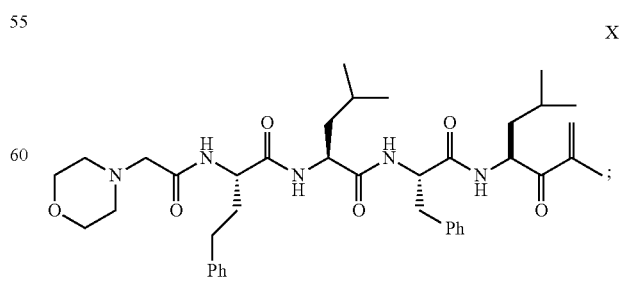

ii. dihydroxylation of compound X

X

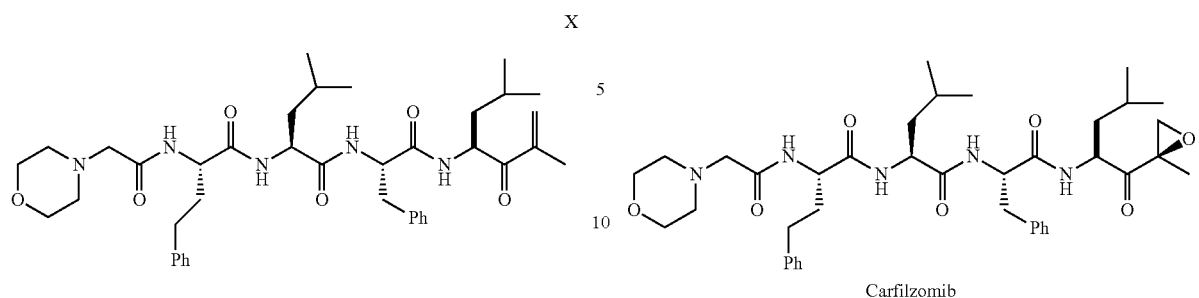

in the presence of chiral dihydroxylating agent to generate compound VIII

VIII

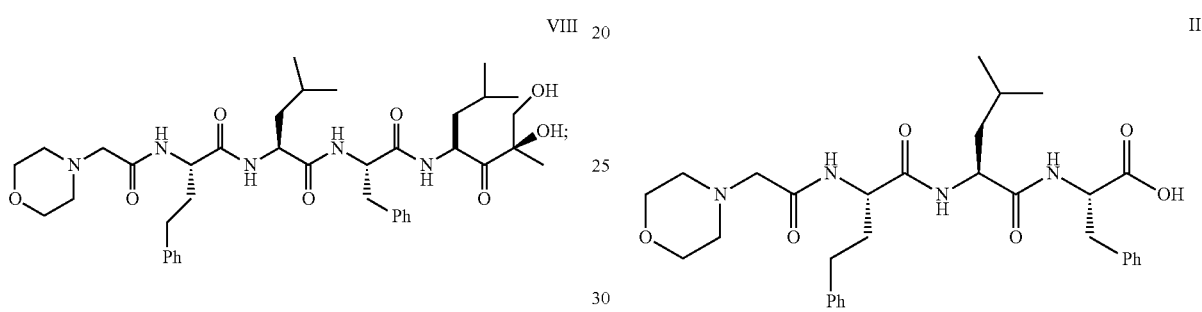

iii. converting the primary hydroxyl of VIII

VIII

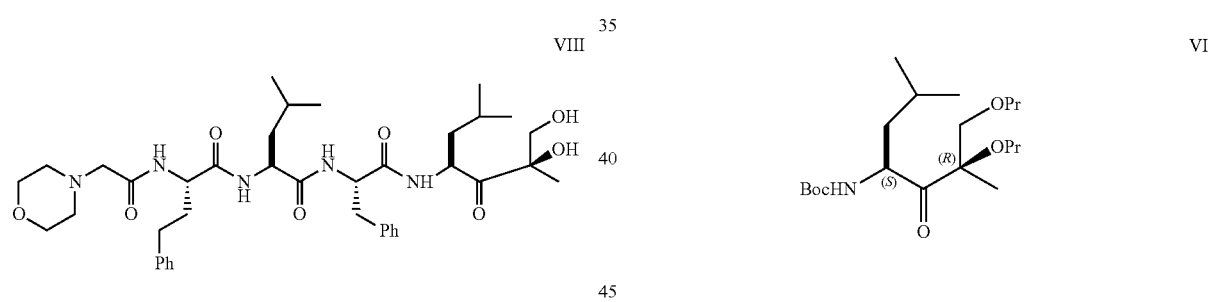

to a leaving group to yield compound IX

IX

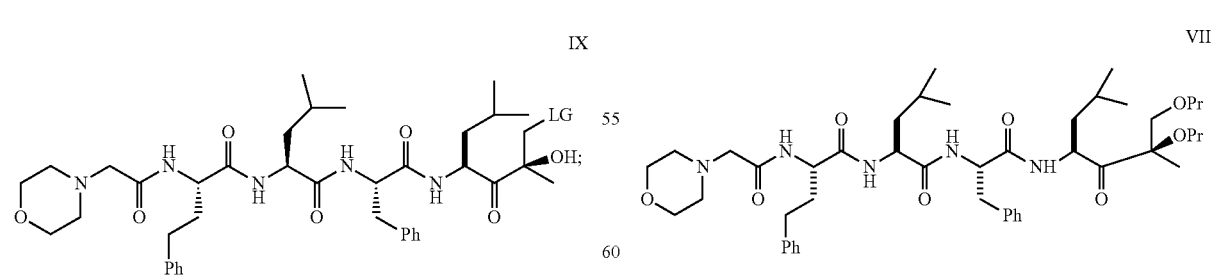

and iv. cyclization of compound IX to Carfilzomib (I) via a base mediated epoxide formation.

2. A process for the preparation of Carfilzomib (I),

Carfilzomib comprising:

i. coupling of a tripeptide of formula II

II with a chiral diol isomer of formula VI

VI in the presence of coupling agent to generate a compound of formula VII

VII wherein the protecting group (Pr) is selected from alkyl, alkoxy, aryl, aralkoxy, and acetyl;

ii. deprotecting the hydroxyl moieties of VII by suitable deprotecting agents to generate a compound of formula VIII

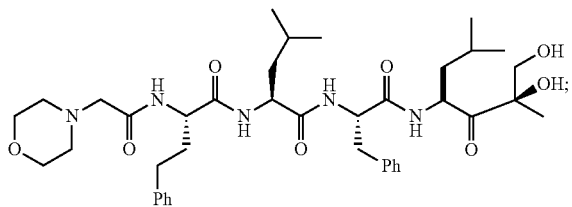
VIII iii. converting the primary hydroxyl of VIII to a leaving group to yield compound IX

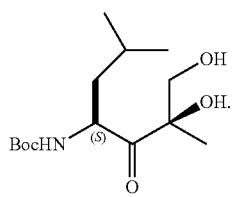
IX and iv. cyclization of IX to Carfilzomib (I) via a base mediated epoxide formation.

3. The process as claimed in claim 1, wherein the Carfilzomib (I) obtained is substantially pure, having an isomeric purity greater than or equal to 99.5%.

4. The process as claimed in claim 2, wherein the Carfilzomib (I) obtained is substantially pure, having an isomeric purity greater than or equal to 99.5%.

5. The process as claimed in claim 1, wherein the compound of formula VIII is prepared by directly coupling a tripeptide of formula II with a chiral diol of formula V in the presence of a coupling agent to generate the compound of formula VIII

V

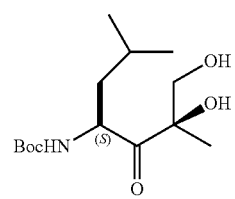

6. A process for the preparation of Carfilzomib (I),

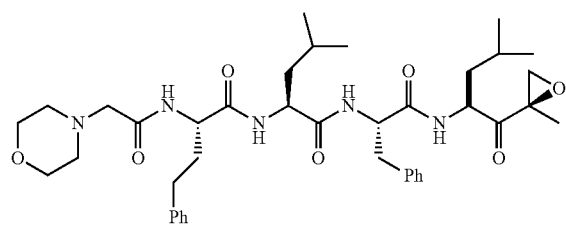
Carfilzomib comprising:

i. coupling of a tripeptide of formula II

II

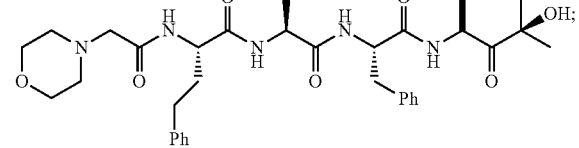

with a chiral diol of formula V

V

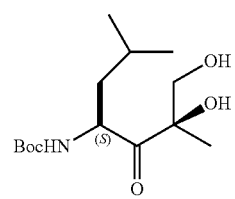

in the presence of a coupling agent to generate VIII

VIII

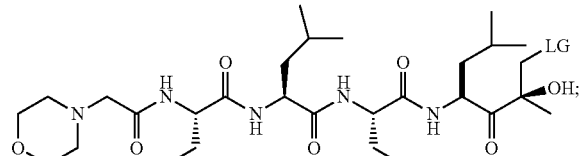

ii. converting the primary hydroxyl of VIII to a leaving group to yield compound IX

IX

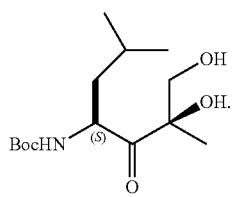

and iii. cyclization of compound IX to Carfilzomib (I) via a base mediated epoxide formation.

* * * * *